(12) United States Patent
Hara et al.

(10) Patent No.: US 8,227,660 B2
(45) Date of Patent: Jul. 24, 2012

(54) ABSORPTIVE ARTICLE

(75) Inventors: Kenji Hara, Sakura (JP); Yasuo Ido, Sakura (JP)

(73) Assignee: Daio Paper Corporation, Ehime (JP)

( * ) Notice: Subject to any disclaimer, the term of this patent is extended or adjusted under 35 U.S.C. 154(b) by 70 days.

(21) Appl. No.: 11/629,239

(22) PCT Filed: Jun. 10, 2005

(86) PCT No.: PCT/JP2005/010679
§ 371 (c)(1),
(2), (4) Date: Dec. 11, 2006

(87) PCT Pub. No.: WO2005/120411
PCT Pub. Date: Dec. 22, 2005

(65) Prior Publication Data
US 2008/0294135 A1   Nov. 27, 2008

(30) Foreign Application Priority Data

Jun. 10, 2004 (JP) ................................ 2004-172505
Jun. 10, 2004 (JP) ................................ 2004-172508

(51) Int. Cl.
*A61F 13/15* (2006.01)
(52) U.S. Cl. .......................... 604/383; 604/380
(58) Field of Classification Search .......... 604/379–380, 604/383
See application file for complete search history.

(56) References Cited

U.S. PATENT DOCUMENTS

| 5,613,960 A | | 3/1997 | Mizutani | |
| 5,830,555 A | * | 11/1998 | Srinivasan et al. | 428/137 |
| 5,895,380 A | * | 4/1999 | Turi et al. | 604/383 |
| 6,022,607 A | * | 2/2000 | James et al. | 428/131 |
| 6,093,871 A | * | 7/2000 | Takai et al. | 604/383 |
| 6,106,925 A | * | 8/2000 | Palumbo | 428/137 |
| 2003/0050618 A1 | * | 3/2003 | Kondo et al. | 604/383 |

FOREIGN PATENT DOCUMENTS

| JP | 2-193663 | 7/1990 |
| JP | 5-228173 | 9/1993 |
| JP | 7-328060 | 12/1995 |
| JP | 8-117277 | 5/1996 |
| JP | 10-272152 | 10/1998 |
| JP | 2003-284740 | 10/2003 |

* cited by examiner

*Primary Examiner* — Lynne Anderson
(74) *Attorney, Agent, or Firm* — Jordan and Hamburg LLP

(57) ABSTRACT

An absorbent article using a surface sheet in which a side of the surface coming into contact with a skin is made of a non-woven fabric and a plastic film layer is stacked in a side of the back of the foregoing non-woven fabric, wherein the residence of a body fluid due to a capillary phenomenon or surface tension in an aperture wall part of the foregoing surface sheet is reduced and the body fluid is rapidly moved into a side of a hydrophilic second sheet or absorber as a lower layer, thereby not only keeping dryness and smoothness on the surface but also preventing turning back with a lapse of time. A surface sheet has a structure in which a side of the surface coming into contact with a skin is made of a non-woven fabric, a plastic film layer is stacked in a side of the back of the foregoing non-woven fabric, and a number of projecting parts and recessing parts are formed by embosses and a number of apertures are formed in the side of the surface coming into contact with a skin; and the foregoing apertures are formed in a proportion so as to have an aperture area of from 0.35 to 0.60 mm$^2$ per aperture and an aperture ratio of from 10 to 19%, and the aperture shape is an aperture shape not having an angledly bent corner.

1 Claim, 7 Drawing Sheets

Fig. 1
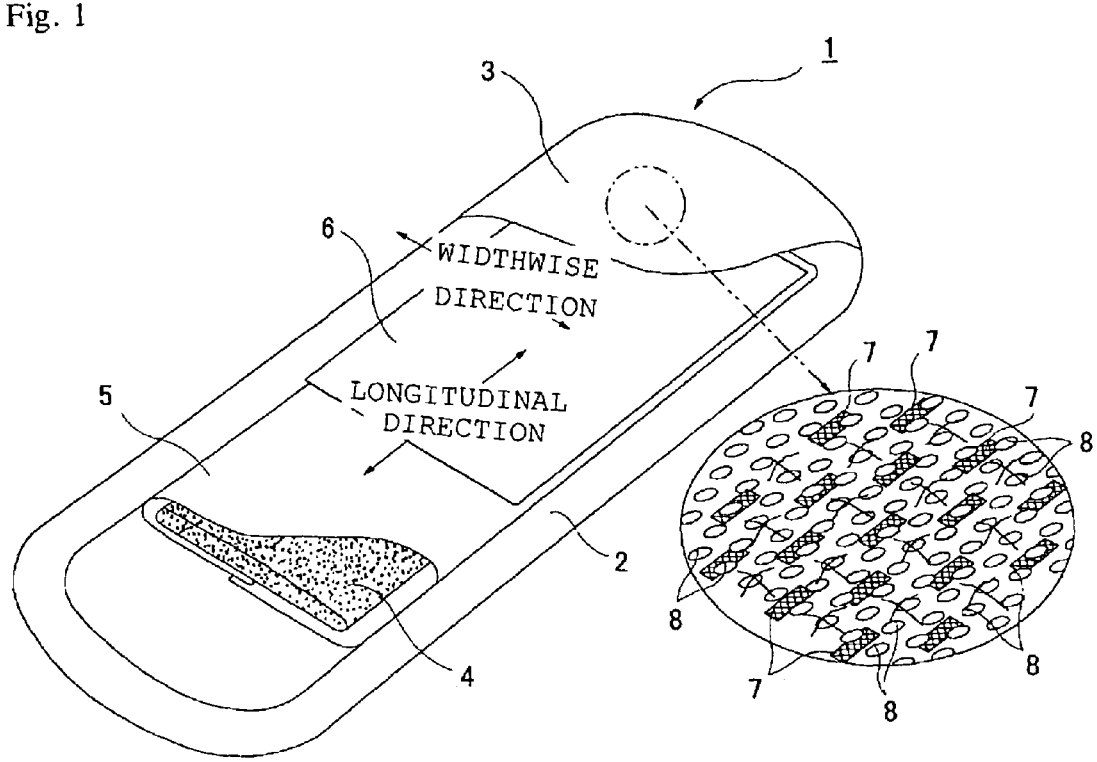
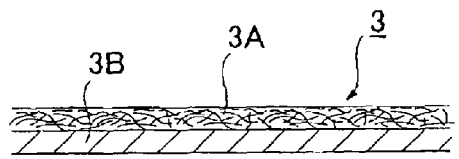
Fig. 2A
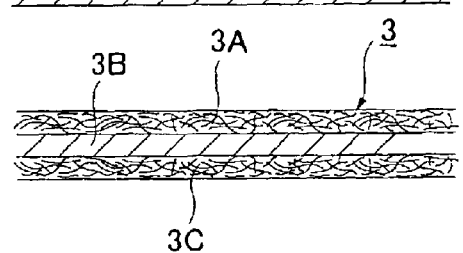
Fig. 2B

ABSORPTIVE ARTICLE

BACKGROUND OF THE INVENTION

The present invention relates to an absorbent article which is used mainly for a sanitary napkin, a virginal discharge sheet, an incontinence pad, a medical pad, toiletries, and so on, and specifically to an absorbent article capable of rapidly absorbing a body fluid, continuously keeping dryness and smoothness on a surface sheet and reducing turning back with a lapse of time.

Hitherto, materials in which an absorber made of cotton-like pulp, etc. is mediated between a liquid impermeable back sheet such as a polyethylene sheet or a polyethylene sheet laminate non-woven fabric and a liquid permeable surface sheet such as a non-woven fabric or a liquid permeable plastic sheet have been known as absorbent articles such as a panty liner, a sanitary napkin, and an incontinence pad.

In the foregoing absorbent articles, for the purposes of not only satisfying with a dry touch to a skin but also increasing the absorption rate of a body fluid, there have been proposed materials in which a heat fusible hydrophobic porous plastic sheet (so-called mesh sheet) is used as the foregoing liquid permeable surface sheet, a hydrophilic sheet called as a second sheet is mediated between the foregoing liquid permeable surface sheet and absorber, and the foregoing mesh sheet and second sheet are discontinuously joined with each other by an embossing pattern. As absorbent articles employing such a configuration, for example, those as described in the following Patent Documents 1 to 3 can be enumerated.

However, in the case where the sheet raw material is a plastic sheet, the surface exhibits film gloss, and a film feeling is given to the skin. Furthermore, in view of such a problem that the plastic sheet tightly attaches to the skin, thereby not only giving a sticky feeling but also disturbing air permeability between the skin and the surface sheet and breathing of the skin, the following Patent Document 4 proposes a surface sheet for sanitary article in which a sheet substrate 50 is made of a fiber layer containing a thermoplastic film layer 50B and a thermoplastic fiber 50A melt joined on the top of the subject film layer, apertures are arranged at prescribed intervals on the foregoing sheet substrate, and a capillary 51 continuously extending downward from a bottom face of the subject sheet substrate on the periphery of the subject aperture is formed, with the foregoing fiber layer being positioned in an inner peripheral surface thereof, as illustrated in FIG. 11.

Furthermore, the following Patent Document 5 proposes a surface material of absorbent article which is provided with peak parts 52 made of a projecting curved surface, bottom parts 53 made of a recessing curved surface, and curved surface-shaped wall parts 54 connecting the subject peak parts 52 and bottom parts 53 to each other and has an infinite number of pore parts 55 formed by the subject peak part 52 and the subject wall part 54 and bottom part 53, with the foregoing wall parts 54 and bottom parts 53 being formed in a film-like structure having a high fiber density and having substantially no liquid permeability, as illustrated in FIG. 12.

Patent Document 1: JP-A-7-328060
Patent Document 2: JP-A-8-117277
Patent Document 3: JP-A-10-272152
Patent Document 4: JP-A-2-193663
Patent Document 5: JP-A-5-228173

PROBLEMS THAT THE INVENTION IS TO SOLVE

However, in the case of the surface sheet for sanitary article according to the foregoing Patent Document 4, by forming the sheet substrate into a sheet material of a multilayered structure made of a thermoplastic film layer and a fiber layer, the defects encountered in the case of using a plastic film as the surface material can be overcome. However, there were involved such problems that the fiber density in the capillary wall part is high and a body fluid remains in the capillary wall part so that it hardly moves into a second sheet or absorber as a lower layer thereof; and that not only a sticky feeling is brought, but also when applied a pressure, the foregoing remaining body fluid is prone to cause turning back.

Similarly, since the surface material according to the foregoing Patent Document 5 has a high fiber density in the bottom part and has a film-like structure, there were some possibilities that a body fluid remains in a pore wall of the pore part due to surface tension; and that not only a sticky feeling is brought, but also when applied a pressure, the foregoing remaining body fluid is prone to cause turning back.

Then, the problem of the invention is to provide an absorbent article using a surface sheet in which a side of the surface coming into contact with a skin is made of a non-woven fabric and a plastic film layer is stacked in a side of the back of the foregoing non-woven fabric, wherein the residence of a body fluid due to a capillary phenomenon or surface tension in an aperture wall part of the foregoing surface sheet is reduced and the body fluid is rapidly moved into a side of a hydrophilic second sheet or absorber as a lower layer, thereby not only keeping dryness and smoothness on the surface but also preventing turning back with a lapse of time.

SUMMARY OF THE INVENTION

In order to solve the foregoing problems, the invention according to a first aspect thereof is to provide an absorbent article having a liquid permeable surface sheet, a back sheet and an absorber mediated between the both sheets, characterized in:

that the foregoing surface sheet has a structure in which a side of the surface coming into contact with a skin is made of a non-woven fabric, a plastic film layer is stacked in a side of the back of the foregoing non-woven fabric, and a number of projecting parts and recessing parts are formed and a number of apertures are formed in the side of the surface coming into contact with a skin; and that the foregoing apertures are formed in a proportion so as to have an aperture area of from 0.35 to 0.60 mm$^2$ per aperture and an aperture ratio of from 10 to 19%, and the aperture shape is an aperture shape not having an angledly bent corner.

In the invention according to the first aspect of the invention, since a sheet substrate in which a side of the surface coming into contact with a skin is made of a non-woven fabric and a plastic film layer is stacked in a side of the back of the foregoing non-woven fabric is used as a surface sheet, neither sticky feeling nor wet feeling is given to the skin, and turning back can be made small. Furthermore, since irregular surface properties having a number of projecting parts and recessing parts are provided in the side of the surface coming into contact with a skin, the contact area with the skin is reduced, thereby giving dryness and smoothness to the skin.

The apertures which are formed in the foregoing surface sheet are formed in a proportion so as to have an aperture area of from 0.35 to 0.60 mm$^2$ per aperture and an aperture ratio of from 10 to 19%, and the aperture shape is an aperture shaped not having an angledly bent corner. That is, by decreasing the aperture ratio and increasing the aperture area as compared with conventional materials and employing an aperture shape capable of readily cutting off a capillary phenomenon or surface tension and not having an angledly bent corner, it is possible to design to reduce a body fluid remaining on the aperture wall surface.

Accordingly, the body fluid rapidly moves into a side of a hydrophilic second sheet or an absorbent as a lower layer without causing residence in the aperture wall parts so that it is possible to keep dryness and smoothness on the surface and to prevent turning back with a lapse of time.

The invention according to a second aspect thereof is to provide the absorbent article of the first aspect of the invention, wherein the foregoing apertures have an oval shape. As the shape of the apertures which are formed in the surface sheet, an oval shape capable of readily cutting off a capillary phenomenon or surface tension is recommended.

The invention according to a third aspect of thereof is to provide the absorbent article of the first aspect of the invention, wherein the foregoing apertures have an oval shape, a minor axis thereof is from 0.7 to 1.3 mm, and a major axis/minor axis ratio is from 1.1 to 1.9. By making the shape of the foregoing apertures have a minor axis of from 0.7 to 1.3 mm and a major axis/minor axis ratio of from 1.1 to 1.9, a capillary phenomenon or surface tension is cut off, and the body fluid is liable to pass therethrough.

The invention according to a fourth aspect thereof is to provide the absorbent article of the first, second or third aspect of the invention, wherein an aperture arrangement pattern where the foregoing apertures are periodically positioned in a projecting peak part of the foregoing surface sheet or in the vicinity thereof is employed.

In the invention according to fourth aspect thereof, an aperture arrangement pattern where the foregoing apertures are periodically positioned in a projecting peak part of the foregoing surface sheet or in the vicinity thereof is employed. Accordingly, the body fluid does not remain in the peak part of the surface sheet, and the dryness and smoothness can be improved.

The invention according to a fifth aspect thereof is to provide the absorbent article of the first through fourth aspect of the invention, wherein a hydrophilic second sheet is provided between the foregoing surface sheet and absorber, and apertures are formed in the foregoing second sheet.

In the invention according to the fifth aspect thereof, a hydrophilic second sheet is provided between the foregoing surface sheet and absorber, and apertures are formed in the foregoing second sheet. In order to increase the absorption rate, the second sheet bears a function to diffuse a body fluid and then absorb it on the absorber. However, in the case of absorbing a large amount of the body fluid, since the body fluid remaining in the second sheet becomes a cause of turning back, by absorbing the body fluid directly on the absorber through the apertures of the second sheet while somewhat sacrificing the absorption rate, an absorption ability of the body fluid increases so that the turning back can be effectively prevented.

The invention according to a sixth aspect thereof is to provide the absorbent article of the fifth aspect of the invention, wherein an aperture arrangement pattern where the apertures formed in the foregoing second sheet and the apertures formed in the foregoing surface sheet are periodically coincident with each other is employed.

By employing an aperture arrangement pattern where the apertures formed in the foregoing second sheet and the apertures formed in the foregoing surface sheet are periodically coincident with each other, the amount of the remaining body fluid in the second sheet can be reduced in a prescribed proportion.

The invention according to a seventh aspect thereof is to provide the absorbent article of the fifth or sixth aspect of the invention, wherein the foregoing surface sheet and second sheet are integrated with each other by a heat fusion joining measure.

By integrating the foregoing surface sheet and second sheet with each other by a heat fusion joining measure, not only irregularities of the surface are made to appear remarkably, but also a soft comfortable feeling is obtained.

The invention according to an eighth aspect thereof is to provide the absorbent article of the first to seventh aspects of the invention, wherein the foregoing surface sheet is of a three-layered structure of non-woven fabric/plastic film/non-woven fabric.

As described above in detail, according to the invention, in an absorbent article using a surface sheet in which a side of the surface coming into contact with a skin is made of a non-woven fabric and a plastic film layer is stacked in a side of the back of the foregoing non-woven fabric, by reducing the residence of a body fluid due to a capillary phenomenon or surface tension in an aperture wall part of the foregoing surface sheet and rapidly moving the body fluid into a side of a hydrophilic second sheet or absorber as a lower layer, it is possible to not only keep dryness and smoothness on the surface but also prevent turning back with a lapse of time.

BRIEF DESCRIPTION OF THE DRAWINGS

FIG. 1 is a partially broken oblique view of a sanitary napkin 1 according to the invention.

FIGS. 2A and 2B illustrate a view to show a sectional structure of a substrate of a liquid permeable surface sheet 3.

DETAILED DESCRIPTION OF THE INVENTION

Figure 3:
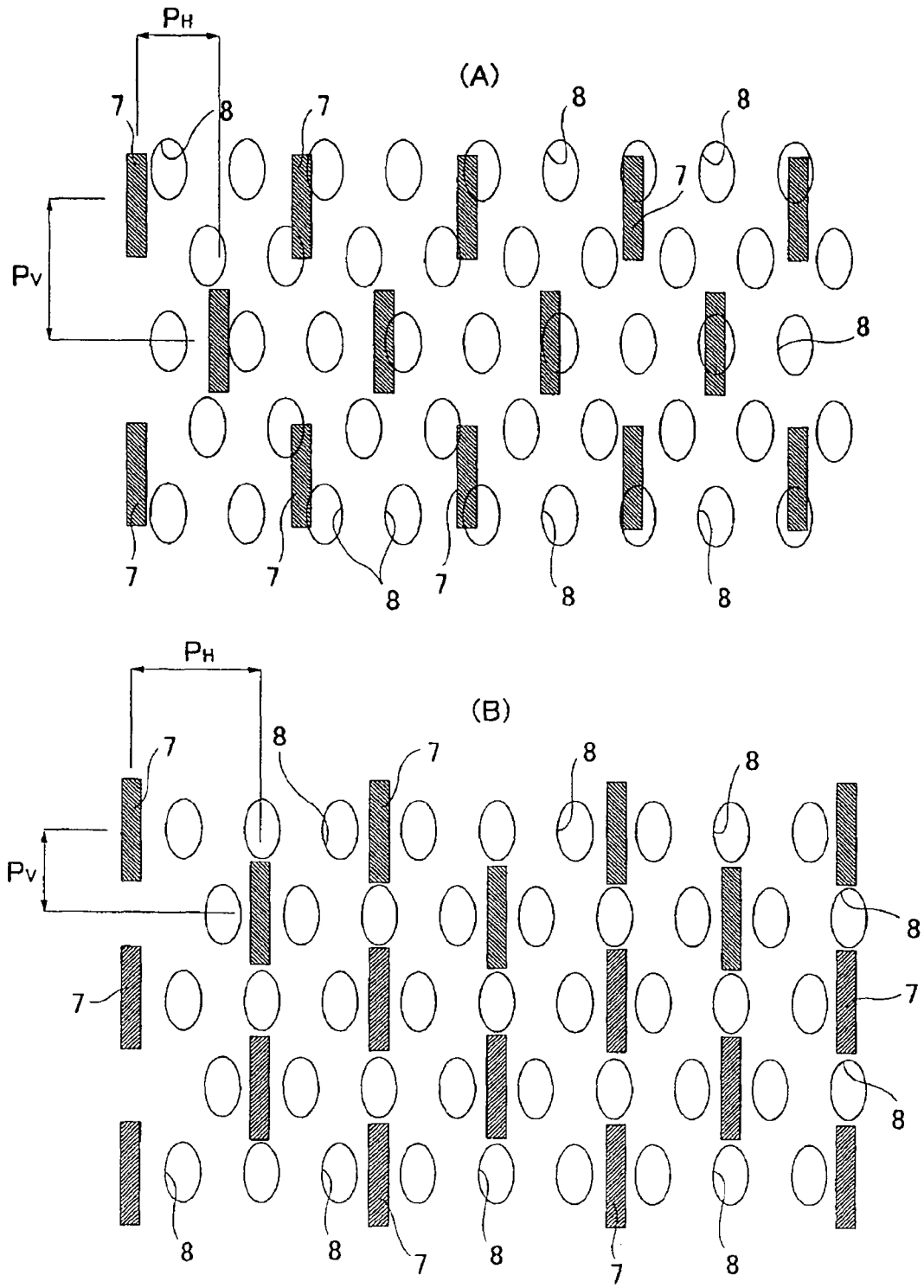
FIG. 3 is a plan view of the principal part to show an emboss and aperture pattern.

Embodiments of the invention will be hereunder described in detail with reference to the accompanying drawings. FIG. 1 is a partially broken oblique view of a thin sanitary napkin 1 according to the invention.

The sanitary napkin 1 is provided mainly for applications such as a panty liner, a sanitary napkin, a virginal discharge sheet, and an incontinence pad and, for example, has a structure as illustrated in FIG. 1 in which not only an absorber 4 or an absorber 4 surrounded by crepe paper 5 as illustrated in the same drawing is mediated between a liquid impermeable back sheet 2 and a liquid permeable surface sheet 3 (hereinafter referred to simply as "surface sheet"), but also a hydrophilic second sheet 6 is arranged between the foregoing surface sheet 3 and absorber 4. In the surroundings of the foregoing absorber 4, the foregoing liquid impermeable back sheet 2 and surface sheet 3 are joined with each other by an adhesive measure such as a hot melt adhesive.

A sheet material at least having water barrier properties such as polyethylene and polypropylene is used for the foregoing liquid impermeable back sheet 2. However, besides, a non-woven sheet which has maintained substantially liquid impermeability by mediating a waterproof film (in this case, the liquid impermeable back sheet is configured of a waterproof film and a non-woven fabric) or the like can be used. In recent years, from the viewpoint of preventing a sweaty phenomenon from occurring, there is a tendency that ones having moisture permeability are suitably used. As such a water barrier/moisture permeable sheet material, a fine porous sheet obtainable by melting and kneading an inorganic filler in an olefin based resin such as polyethylene and polypropylene to mold a sheet and then uniaxially or biaxially stretching it is suitably used.

In the invention, in particular, a surface sheet having a structure in which a side of the surface coming into contact with a skin is made of a non-woven fabric, a plastic film layer is stacked at least in a side of the back of the foregoing non-woven fabric, and a number of projecting parts and recessing parts are formed and a number of apertures are formed in the side of the surface coming into contact with a skin is used as the foregoing surface sheet 3.

Concretely, a sheet of a two-layered structure composed of hydrophobic non-woven fabric 3A/plastic film 3B as illustrated in FIG. 2(A), or a sheet substrate of a three-layered structure composed of hydrophobic non-woven fabric 3A/plastic film 3B/hydrophobic non-woven fabric 3C or a sheet substrate of a three-layered structure composed of hydrophobic non-woven fabric 3A/plastic film 3B/hydrophilic non-woven 3C as illustrated in FIG. 2(B) can be used. And a surface sheet obtained by giving dot-like embossing in a fine pattern, whereby not only the surface properties are made to have irregular surface properties such that a number of projecting parts and recessing parts are formed, but also a number of apertures are formed so as to penetrate from the surface side through the back, is used.

As a raw material fiber which constitutes the foregoing non-woven fabrics 3A and 3C, for example, synthetic fibers such as olefin bases, for example, polyethylene and polypropylene, polyester bases, and polyamide bases, and besides, regenerated fibers such as rayon and cupra and natural fibers such as cotton can be enumerated; and non-woven fabrics obtainable by an appropriate processing method such as an air-through method, a spun lace method, a spun bond method, a thermal bond method, a melt brown method, and a needle punch method can be used. Of these processing methods, the spun lace method is excellent in view of rich flexibility and draping properties; and the air-through method and the thermal bond method are excellent in view of bulkiness and softness. Though the fiber of the non-woven fabric may be any of a long fiber or a short fiber, it is suitable to use a short fiber because it brings texture of toweling. Furthermore, in order to make it easy to perform the embossing method, it is suitable to use an olefin based fiber such as relatively low-melting polyethylene or polypropylene. Moreover, composite fibers such as a core-sheath type fiber in which a fiber with a high melting point is used as a core, whereas a fiber with a low melting point is used as a sheath; a side-by-side type fiber; and a divided type fiber can also be suitably used. Of these, a non-woven fabric containing a divided type composite fiber is especially desired. The divided type composite fiber is a non-woven fabric containing a wholly or partially dividable composite fiber and having a fine fiber surface and can be suitably used as a material capable of meeting the purpose of this application because it is especially excellent in touch. In this case, it is desired to contain a divided type composite fiber in a proportion of from 5 to 40% by weight and a heat fusible fiber in a proportion of from 60 to 95% by weight. When the content of the foregoing divided type composite fiber is less than 5%, the desired softness and texture cannot be obtained. Also, when it exceeds 40% by weight, fluffing is liable to occur due to friction, and therefore, such is not preferable.

On the other hand, as a raw material of the foregoing plastic sheet 3B, for example, olefin based resins such as polyethylene and polypropylene, polyesters, polyamide based resins such as nylons, and an ethylene-vinyl acetate (EVA) copolymer can be used.

In the present surface sheet 3, as illustrated in FIGS. 3(A) and 3(B), in such a sheet substrate, not only embosses 7, 7 . . . having a specified shape, in the illustrated examples, longitudinal rectangular embosses 7, 7 . . . , are imparted, but also a number of apertures 8, 8 . . . having a specified shape are formed, and the resulting surface sheet is used as a surface material of the absorbent article 1. Incidentally, for the purpose of forming the foregoing apertures 8, there are suitably employed a method in which in a state that a synthetic resin sheet is softened in the vicinity of the softening temperature and positioned on an upper surface of a support having a number of apertures, sucking is performed from a lower part of the support or pressurization is performed by an air pressure from an upper surface of the support, thereby forming apertures, and a method of sticking heated needles.

With respect to a pattern of the foregoing embosses 7 and a pattern of the apertures 8, in the example as illustrated in FIG. 3(A), the embosses 7, 7 . . . are arranged in a zigzag state; the foregoing apertures 8, 8 . . . are similarly arranged in a zigzag state; and the relative positional relationship of these embosses 7, 7 . . . and apertures 8, 8 . . . is arranged in a pattern not having regularity. Furthermore, in the example as illustrated in FIG. 3(B), the embosses 7, 7 . . . are arranged in a zigzag state; the foregoing apertures 8, 8 . . . are similarly arranged in a zigzag state; and the relative positional relationship of these embosses 7, 7 . . . and apertures 8, 8 . . . is arranged in a pattern such that the embosses 7, 7 . . . and the apertures 8, 8 . . . do not superpose on each other and that the apertures 8 are positioned in a projecting peak part formed by the foregoing embosses 7, 7 . . . or in the vicinity thereof. With respect to the shape of the foregoing embosses 7, in order that irregularities may readily appear on the surface, a long, narrow short linear emboss in which a vertical dimension and a horizontal dimension largely differ from each other is desired. The shape of this linear emboss may be, for example, arranged so as to have a vertical dimension of 3 mm, a horizontal dimension of 1 mm, a pitch in a horizontal direction ($P_H$) of from 3 to 8 mm, and a pitch in a vertical direction ($P_V$) of from about 3 to 5 mm.

Figure 4:
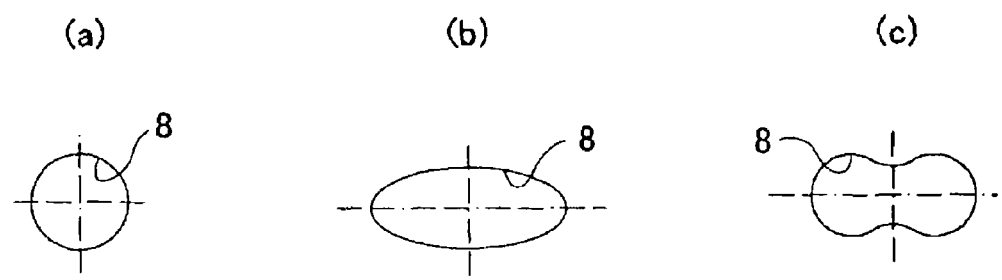
FIG. 4 is a view to show a shape example of an aperture 8 not having an angledly bent corner.

For the purpose of reducing the residence of a body fluid due to a capillary phenomenon or surface tension in an aperture wall part of the surface sheet 3, examples of the shape of the apertures 8 to be formed in the foregoing surface sheet 3 include an aperture shaped not having an angledly bent corner, specifically circular, oval, cocoon type and special cocoon type shapes as illustrated in FIG. 4. Incidentally, an aperture shape of an even-numbered polygon, for example, a regular square and a hexagon, is excluded from the invention because the body fluid is liable to remain in the angledly bent corner due to surface tension. Of the apertures shapes not having an angledly bent corner, an oval shape is especially preferable. In the case of an oval shape, since it has a minor axis and a major axis, with a degree of surface tension being different in the respective axes, whatever the body fluid remains in an aperture wall part, a water film is liable to be broken due to imbalance of the surface tension balance, and the body fluid readily passes through the apertures 8. In this case, it is desired that the foregoing minor axis is from 0.7 to 1.3 mm, with a major axis/minor axis ratio being from 1.1 to 1.9, and preferably from 1.6 to 1.8.

Furthermore, the foregoing apertures 8 are formed in a proportion so as to have an aperture area of from 0.35 to 0.60 mm$^2$, and preferably from 0.47 to 0.54 mm$^2$ per aperture and an aperture ratio of from 10 to 19%, and preferably from 11 to 14%. When the foregoing aperture area is less than 0.35 mm$^2$, the aperture area is too small so that the surface tension or capillary phenomenon cannot be cut off, whereby the body fluid remains in the aperture wall part. Also, when the aperture area exceeds 0.60 mm$^2$, turning back of the body fluid through the apertures is generated, and therefore, such is not preferable. On the other hand, when the aperture ratio is less than 10%, the aperture ratio is too small so that the body fluid which has been discharged onto the surface cannot be rapidly permeated. Also, when it exceeds 19%, turning back of the body fluid is generated, and therefore, such is not preferable.

Incidentally, the shape of the sheet penetration direction of the apertures 8 may be formed in a tapered state such that the aperture area is enlarged step by step or in a reverse tapered state such that the aperture area is reduced step by step, in addition to a straight shape.

Figure 8:
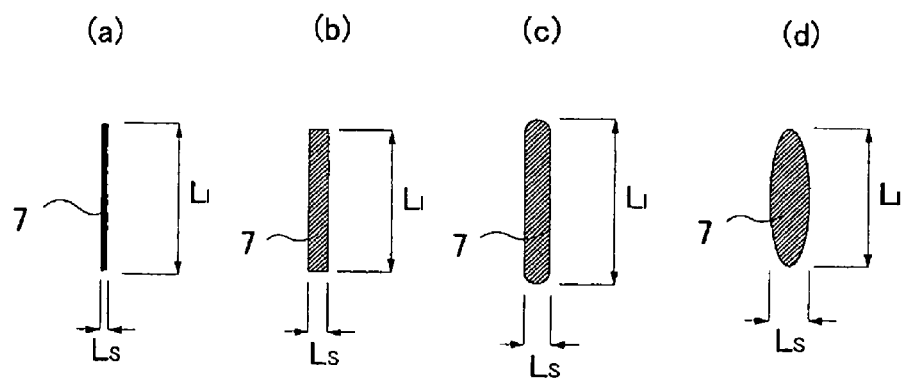
FIG. 8 is a view to show a shape example of an emboss 7.

On the other hand, as the foregoing embosses 7 having a long, narrow shape, for example, a linear shape, a long, narrow rectangular shape, an oval rectangular shape in which the front and rear ends of this long, narrow rectangle are formed in an arc state, and an oval shape having a large major axis/minor axis ratio as illustrated in FIGS. 8(*a*) to 8(*d*) can be enumerated. It is desired that these embosses 7 have a dimension in a longitudinal direction ($L_l$) of from 2 to 5 mm, and preferably from 2.5 to 3.5 mm and a dimension in a short direction ($L_s$) of from 0.2 to 2.0 mm, and preferably from 0.5 to 1.5 mm.

By forming the foregoing embosses 7 in a long, narrow shape and making the dimension in a widthwise direction small as far as possible, it is possible to reduce a "burr" feeling felt when the absorbent article is traced with a finger in the longitudinal direction of the absorbent article. Also, because of the matters that the direction of a recessing groove follows the absorbent article and that the foregoing embosses are arranged in a zigzag arrangement pattern, a feeling of resistance due to the irregularities is homogenized so that a smooth feeling of the surface sheet 3 is improved and that the touch and texture are improved.

It is desired that the foregoing embosses 7, 7 . . . have an area ratio of from 5 to 14%. When the area ratio is less than 5%, it is difficult to form remarkable irregularities on the surface sheet 3. Also, when it exceeds 15%, it is impossible to smoothen the irregular surface properties due to the proportional correlation between the emboss area ratio and resistivity. Moreover, with respect to the intervals of the zigzag arrangement pattern of the foregoing embosses 7, 7 . . . , it is desired that the pitch in a vertical direction ($P_V$) is from 3 to 7 mm, and preferably from 3 to 5 mm and that the pitch in a horizontal direction ($P_H$) is from 3 to 10 mm, and preferably from 4 to 7 mm.

Figure 9:
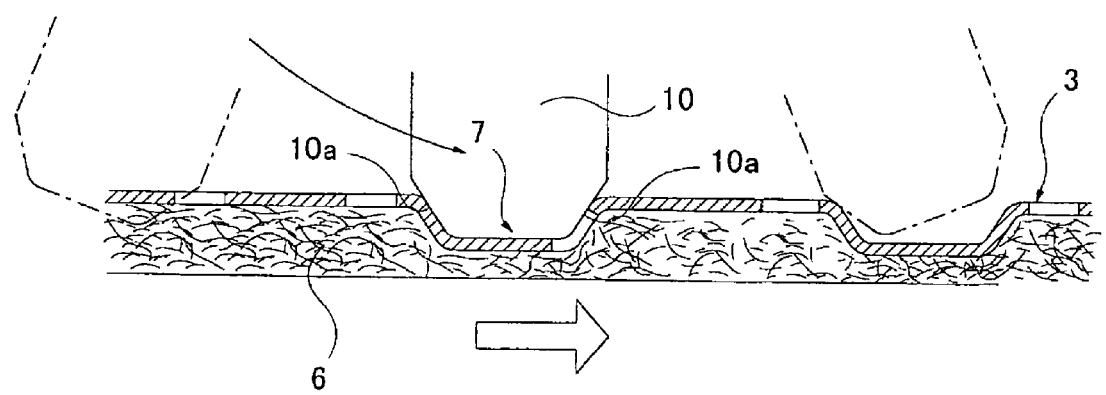
FIG. 9 is a view of an embodiment of imparting an emboss by an embossing roller 10.

The formation of the embosses 7, 7 . . . on the surface sheet 3 is carried out by passing the sheet between an embossing roller having projecting parts formed on the surface thereof and an anvil roller. On this occasion, in order to reduce or eliminate a "burr" as generated when the foregoing projecting part is absorbed in the sheet and thereafter comes out from the sheet, it is desired that in an embossing roller for imparting the embosses 7, 7 . . . , chamfering parts 10*a*, 10*a* in an inclined shape are respectively provided in the front and rear parts in a rotational direction in a tip of a projecting part 10 as illustrated in FIG. 9. By providing the foregoing chamfering parts 10*a*, 10*a*, as illustrated in the same drawing, when the embossing projecting part 10 comes out from the emboss 7, it does not scrape up the fibers outwards and smoothly comes out from the emboss 7 so that the generation of a "burr" can be inhibited.

Figure 10:
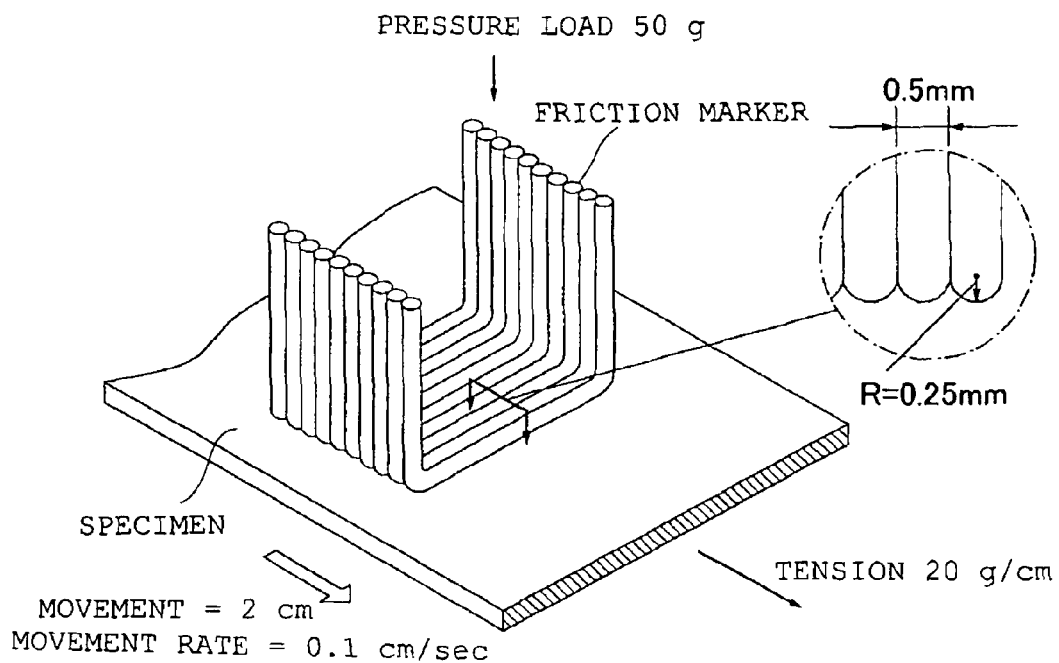
FIG. 10 is a view to show the point of an MIU test.
Figure 11:
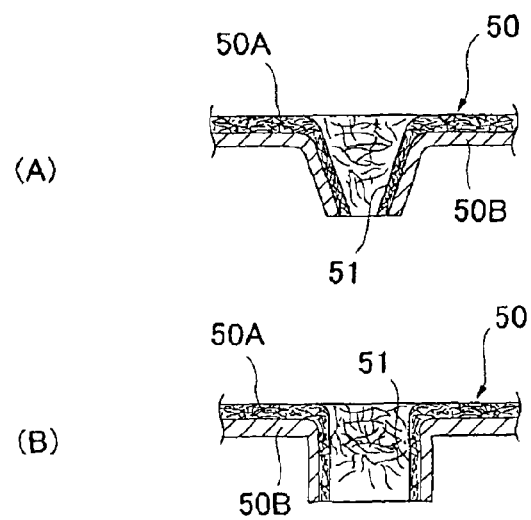
FIG. 11 is a view to show a sectional view of an aperture of a surface sheet according to a conventional example (No. 1).
Figure 12:
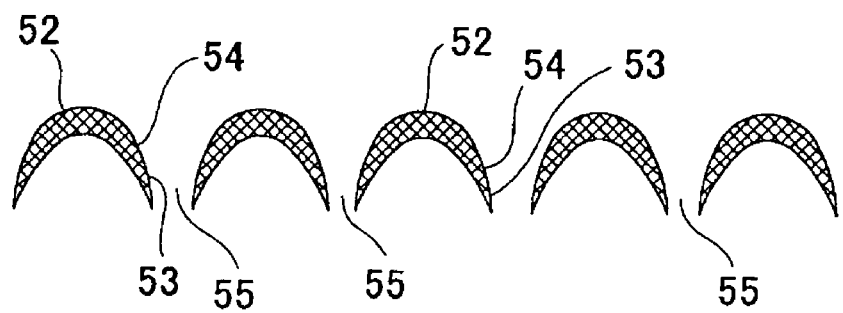
FIG. 12 is a view to show a sectional view of an aperture of a surface sheet according to a conventional example (No. 2).

With respect to the surface sheet 3 having embosses 7, 7 . . . and apertures 8, 8 . . . formed therein as described previously, it is desired that its coefficient of friction (MIU) in the side of the surface coming into contact with a skin is not more than 0.3 in a product state thereof. As illustrated in FIG. 10, the foregoing coefficient of friction (MIU) is measured by using a friction tester, KES-SE (manufactured by Kato Tech Co., Ltd.), arranging ten contact makers obtainable by folding a piano string having a diameter of 0.5 mm in a U-shape, bringing a contact surface into press contact with a specimen at a force of 50 gf by a weight under a condition at a sensitivity of 25 gf/v, moving this specimen 2 cm in a horizontal direction at a fixed rate of 0.1 cm/sec, measuring a coefficient of friction in a moving region and a standard deviation of coefficient of friction in three points in a vertical direction, respectively and determining its average value, thereby determining an MIU value.

As the absorber 4 which is mediated between the foregoing liquid impermeable back sheet 2 and surface sheet 3, for example, one having a highly water absorbent resin mixed in pulp or one having a chemical fiber mixed in pulp and having a highly water absorbent resin mixed therein is used. It is desired that the foregoing absorber 4 is surrounded by the crepe paper 5 as illustrated in the drawing for the purposes of not only keeping the shape and rapidly diffusing menstrual blood or the like but also preventing turning back of the menstrual blood or the like which has been once absorbed. Examples of the foregoing pulp include chemical pulps obtained from wood, pulps made of a cellulose fiber such as molten pulp, and pulps made of an artificial cellulose fiber such as rayon and acetate. Conifer pulps having a long fiber length are more suitably used from the standpoints of functions and costs rather than broad-leaved tree pulps.

Examples of the foregoing highly water absorbent resin include a polyacrylic acid salt crosslinked material, a self-crosslinked polyacrylic acid salt, a saponified material of an acrylic ester-vinyl acetate copolymer crosslinked material, an isobutylene maleic anhydride copolymer crosslinked material, a polysulfonic acid salt crosslinked material, and a partially crosslinked material of a water swellable polymer such as polyethylene oxide and polyacrylamide. Of these, acrylic acid or acrylic acid based materials which are excellent in water absorption amount and water absorption rate are suitable. In a manufacturing process of the foregoing highly water absorbent resin having a water absorption performance, it is possible to adjust the water absorption power and water absorption rate by adjusting a crosslinking density and a crosslinking density gradient. The content of the foregoing highly water absorbent resin is desirably from 10 to 60%. When the content of the highly water absorbent resin is less than 10%, a sufficient absorption ability cannot be given, whereas when it exceeds 60%, the entanglement between pulp fibers is not found and the sheet strength is lowered so that breakage, fracture, or the like is likely generated.

The hydrophilic second sheet 6 which is arranged between the foregoing liquid permeable surface sheet 3 and absorber 4 is only required to have hydrophilicity against a body fluid. Concretely, a material obtainable by bringing hydrophilicity to a raw material per se by using a regenerated fiber such as rayon and cupra or a natural fiber such as cotton can be used, or a fiber obtainable by surface treating a synthetic fiber such as olefin bases, for example, polyethylene or polypropylene, polyester bases, and polyamide bases with the hydrophilic agent, thereby imparting hydrophilicity can be used.

Figure 6:
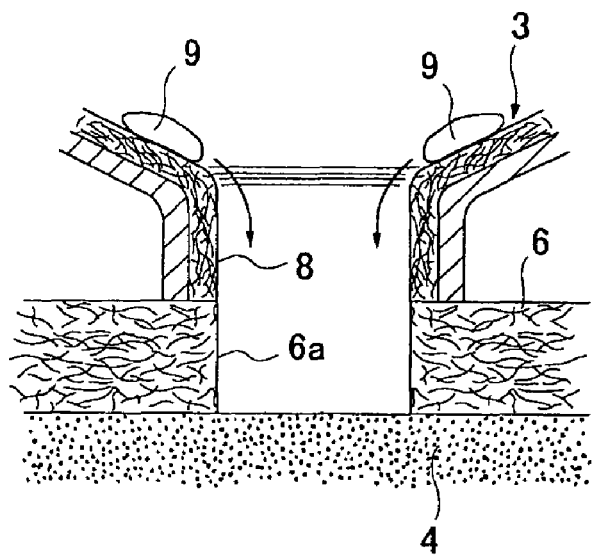
FIG. 6 is an explanatory view (No. 2) of the absorption mechanism of a body fluid.

As the foregoing hydrophilic second sheet 6, a material obtainable by forming apertures 6a in a prescribed pattern as illustrated in FIG. 6 may be used. In this case, though it is not always necessary to make the apertures 6a formed in the second sheet 6 and the apertures 8 formed in the surface sheet 3 completely coincident with each other, an aperture arrangement pattern where the apertures 6a formed in the foregoing second sheet 6 and the apertures 8 formed in the foregoing surface sheet 3 are at least periodically coincident with each other is desirable.

Furthermore, it is desired that the foregoing second sheet 6 is discontinuously joined with the surface sheet 3 by hot melt or heat fusion (embossing). Also, the embossing processing may be applied from the surface side (the side of the liquid permeable surface sheet 3) or the back side (the side of the second sheet 6) in a stacked state of the both sheets as it stands and according to circumstances, may be applied simultaneously from the surface side and the back side. By applying embossing in a stacked state of the both sheets as it stands, not only irregularities of the surface are made to appear more strongly, but also a soft comfortable feeling is brought.

Next, the absorption mechanism in the present absorption article will be described in detail.

Figure 5:
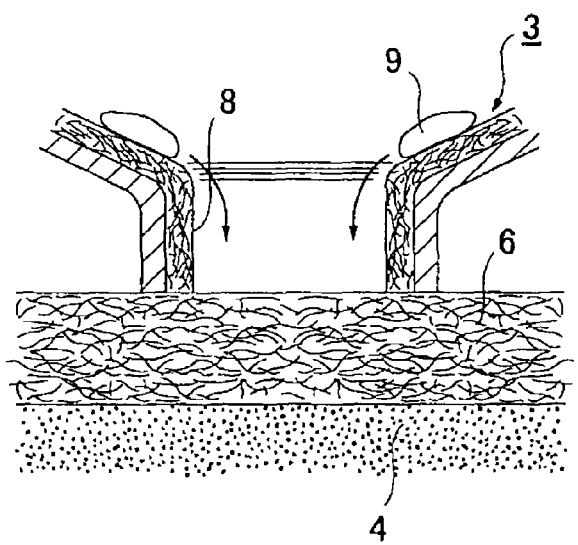
FIG. 5 is an explanatory view (No. 1) of the absorption mechanism of a body fluid.

First of all, an example as illustrated in FIG. 5 is a structural example in which the second sheet 6 is provided in a lower layer of the surface sheet 3 made of a two-layered structure. A body fluid 9 which has been discharged onto the surface sheet 3 passes through the apertures 8 and reaches the second sheet 6, and after being diffused here, is absorbed onto the absorber 4. In the foregoing apertures 8, the body fluid 9 passes therethrough due to a surface tension or capillary phenomenon without remaining on the aperture wall surface and reaches the second sheet 6. Thus, the body fluid 9 is absorbed onto the second sheet 6 at a high absorption rate and thereafter absorbed onto the absorber 4.

An example as illustrated in FIG. 6 is a structural example in the case where the apertures 6a formed in the second sheet 6 and the apertures 8 formed in the surface sheet 3 are made coincident with each other. Usually, in the case of having the second sheet 6, the body fluid 9 is rapidly absorbed by this second sheet 6 and diffused, and absorbed onto the absorber 4 at a slight time difference. However, when the body fluid 9 gradually remains in a portion of the second sheet 6 facing on the apertures 8 of the surface sheet 3 and becomes in a state that the body fluid 9 is stored to some extent, turning back is likely generated. As in the present example, in the case where the apertures 6a of the second sheet 6 and the apertures 8 of the surface sheet 3 are made coincident with each other, though immediately after the body liquid 9 has flowed into the apertures 8, the absorption rate drops, when a prescribed period of time elapses, the body fluid 9 is absorbed onto the absorber 4 having markedly high absorption ability and holding ability as compared with the second sheet 6. Thus, even when a large amount of the body fluid 9 is absorbed, turning back is hardly generated.

Figure 7:
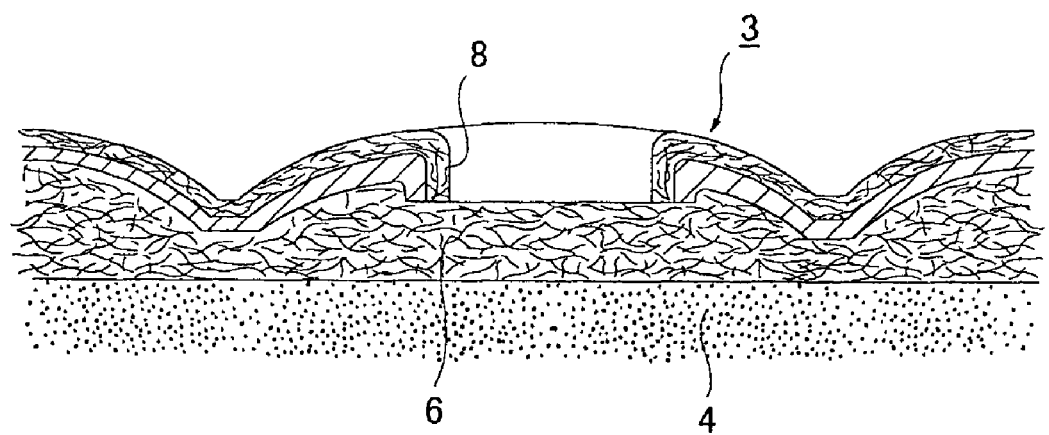
FIG. 7 is an explanatory view (No. 3) of the absorption mechanism of a body fluid.

Next, an example as illustrated in FIG. 7 is an example of a structure in which joining between the surface sheet 3 and the second sheet 6 is carried out by applying embossing processing from the surface side in a stacked state of the both sheets as it stands, thereby integrating the both with each other. In this case, the body fluid 9 is also absorbed on the absorber 4 via the second sheet 6 according to an absorption embodiment the same as in the foregoing absorption mechanism as illustrated in FIG. 5.

Examples

Three kinds of a surface sheet according to Example 1, Example 2 and Comparative Example as shown in the following Table 1 were prepared; apertures were formed in specifications as shown in the same table; 3 cc of artificial menstrual blood was poured; and an absorption rate test and a turning back test were carried out.

In the absorption rate test, the evaluation was made in terms of a time (s) until 3 cc of artificial menstrual blood was absorbed; and in the turning back test, 3 cc of artificial menstrual blood was poured onto a napkin using each sample sheet, filter paper was placed under a load of 100 g, and in each of the cases after a lapse of 10 seconds and after a lapse of 5 minutes, the amount of turning back was measured.

TABLE 1

|  |  | Example 1 | Example 2 | Comparative Example |
|---|---|---|---|---|
| Sheet substrate | Layer structure | Two layers | Three layers | Three layers |
|  | First layer non-woven fabric | 13 | 15 | 17 |
|  | Second layer film | 20 | 7 | 7 |
|  | Third layer non-woven fabric | — | 12 | 14 |
|  | Basis weight (g/m$^2$) | 33 | 34 | 38 |
|  | Kind of fiber | PP/PE | PP/PE | PP |
| Specifications of aperture | Shape | Oval shape | Oval shape | Lattice shape |
|  | Major axis (mm) | 2.1 | 1.3 | 1.1 (vertical) |
|  | Minor axis (mm) | 1.3 | 0.7 | 1.1 (horizontal) |
|  | Major axis/minor axis | 1.6 | 1.8 | 1.0 (aspect ratio) |
|  | Aperture ratio (%) | 14 | 11 | 21 |
|  | Area (mm$^2$) | 0.54 | 0.47 | 0.34 |
|  | Pattern of embossing | Vertical Pitch: 3.5 mm | Vertical Pitch: 3.5 mm | Vertical Pitch: 3.5 mm |
|  | Interfacial coating | 3% - 4.2 g/m$^2$ | 3% - 4.2 g/m$^2$ | 3% - 4.2 g/m$^2$ |

TABLE 1-continued

|  |  | Example 1 | Example 2 | Comparative Example |
|---|---|---|---|---|
| Test result | Absorption rate (s) | 1.40 | 1.11 | 1.49 |
|  | Turning back after a lapse of 10 seconds (cc) | 0.007 | 0.007 | 0.004 |
|  | Turning back after a lapse of 5 minutes (cc) | 0.110 | 0.060 | 0.127 |

The invention claimed is:

1. An absorbent article, comprising:

a longitudinal axis defining a longitudinal direction of the absorbent article;

a liquid permeable surface sheet;

a back sheet joined with the liquid permeable surface sheet; and an absorber mediated between said liquid permeable surface sheet and said back sheet, said liquid permeable surface sheet having a structure in which a side of said surface coming into contact with a skin is made of a non-woven fabric, a plastic film layer is stacked in a side of the back of said non-woven fabric, and longitudinal rectangular embosses in a zigzag arrangement pattern are formed in a longitudinal direction of said absorbent article so that each of said embosses comprises a pair of longitudinally extending sides extending in said longitudinal direction of said absorbent article and a pair of sides respectively extending transversely relative to said longitudinally extending sides, said longitudinally extending sides being longer than said transversely extending sides, said embosses comprising a number of projecting parts and recessing parts, and said structure includes elliptical apertures, all of said elliptical apertures being arranged so that their major axes extend only in said longitudinal direction of said absorbent article and are formed in the side of the surface coming into contact with a skin, said apertures being in a zigzag arrangement pattern in a longitudinal direction of said absorbent article so that any given aperture and said given aperture's nearest adjacent aperture at a different longitude in said longitudinal direction of said absorbent article are laterally offset, and said apertures are positioned therealong the longitudinal direction of the absorbent article and relative to the embosses so that the recessing parts of the embosses do not entirely overlap the apertures and the apertures are either on top of or adjacent to projecting parts of one or more of the embosses, said apertures being formed in a proportion so as to have an aperture area of from 0.35 to 0.60 mm$^2$ per aperture and an aperture ratio of from 10 to 19%, and the aperture shape is an aperture shape not having an angledly bent corner;

wherein each of the longitudinally extending sides of the rectangular embosses comprises a longitudinal length ranging from 2 to 5 mm., and each of the transversely extending sides of the rectangular embosses comprises a transversely extending length ranging from 0.2 to 2.0 mm.

* * * * *